(12) United States Patent
Beals, Jr. et al.

(10) Patent No.: US 6,199,433 B1
(45) Date of Patent: Mar. 13, 2001

(54) GASKET ADHESION TEST GRIP TOOL

(75) Inventors: Harry C. Beals, Jr., Jackson; Claude W. Duvall, Flanders; Ralph Liguori, Oakland; Ronald B. Walsh, Hacketstown, all of NJ (US)

(73) Assignee: Lucent Technologies Inc., Murray Hill, NJ (US)

( * ) Notice: Subject to any disclaimer, the term of this patent is extended or adjusted under 35 U.S.C. 154(b) by 0 days.

(21) Appl. No.: 09/271,344

(22) Filed: Mar. 18, 1999

(51) Int. Cl.[7] .................................................. G01N 3/08

(52) U.S. Cl. .................................. 73/831; 73/856; 29/758

(58) Field of Search .............................. 73/826, 827, 831, 73/834, 856; 29/758

(56) References Cited

U.S. PATENT DOCUMENTS

| 4,583,287 | * | 4/1986 | McDevitt et al. | 29/741 |
| 4,605,256 | * | 8/1986 | Stokoe | 294/99.2 |
| 4,660,281 | * | 4/1987 | Omand | 29/764 |
| 4,787,139 | * | 11/1988 | Sweet | 29/758 |

* cited by examiner

*Primary Examiner*—Max Noori

(57) ABSTRACT

A tool for verifying the wetting of a "Hollow D" gasket adhesive sealing a panel, door or cabinet frame substrate and the like, including a pair of substantially symmetrical gripping surfaces having upper portions fastened together to receive a force gauge for measuring the upwards pulling on the gasket, and also having lower portions with inwardly facing extensions of a thickness equal to or less than that of the adhesive carrier for grasping the gasket when in place, and with a spacing between the facing extensions equal to or greater than the width of the adhesive carrier of the gasket.

15 Claims, 3 Drawing Sheets

GASKET ADHESION TEST GRIP TOOL

BACKGROUND OF THE INVENTION

1. Field of the Invention

This invention relates to gaskets used to seal panels, doors or cabinet frames, in general, and to "Hollow D" gaskets commonly employed to seal against leakage of electromagnetic radiation from enclosed electronic equipment, and against the incursions of snow, sleet and rain into the housings where such equipment is operating, in particular.

2. Description of the Related Art

As is well known and understood, such gaskets are commonly employed in housed Personal Communication Systems and similar cellular Base Stations, and are typically of a type having an adhesive strip on its back surface that is rolled against the door and/or frame in sealing the housing. As is also appreciated, need frequently arises to maintain or service the electronic equipment within the housing, resulting in the necessary repetitive opening and closing of these various panels, doors and cabinets. In use, however, it has been found that the gaskets do not adequately adhere to the edge surface—frequently because the pressure applied when initially installing the gasket is improper. That is, when an insufficient amount of pressure is applied through the conventional type of roller employed, there is an insufficient contact between the edge surface and the adhesive strip on the back of the gasket. Conversely, applying an excessive amount of pressure damages the gasket itself. In both these instances, a very real tendency exists for the gasket to eventually peel away from the panel, door or cabinet frame involved.

Considering the problem, a realization became apparent that something was needed to verify that the wetting of the "Hollow D" gasket adhesive was sufficient, and in a non-destructive manner. In other words, something was required other than merely grabbing the side areas of the gasket and pulling upwards until the adhesive tore away, as that obviously destroyed the usefulness of the gasket.

SUMMARY OF THE INVENTION

As will become clear from the following description, a gasket adhesion test grip tool which satisfies this requirement operates to apply an upwards perpendicular force upon the adhesive area of the gasket, along with a design profile which is able to verify the wetting along the entire width of the adhesive. As will be seen, the dimensions of the test grip tool are selected so as to cooperate in this manner with the various widths of gaskets used for the sealing purpose.

Thus, and in accordance with the invention, a gasket adhesion test grip tool includes a pair of pliable surfaces having upper portions fastened together and lower portions spaced apart a distance at least equal to the width of the "Hollow D" gasket. As set forth, each of the upper portions are symmetrical, and couple with a force measuring gauge for the upwards pulling on the gasket which is positioned at a location over the adhesive strip and equidistant between the side areas of the gasket. With each of the pliable surfaces having facing ends at their lower portions separated by a distance equal to or greater than the width of the adhesive carrier, a perpendicular upward force can be applied to verify the wetting of the adhesive by the gauge, without going so far as to potentially damage the gasket.

To assure an accurate reading of the verification obtained with the gauge, included apertures on the upper surface portions are arranged colinearly, with each being located at a point equidistant from the facing ends of the lower surface portions. In accordance with the preferred embodiment set forth, furthermore, the pair of pliable surfaces are designed substantially symmetrical both in configuration and in dimension—and, so as to facilitate manufacture of the test grip tool and accuracy in its deployment, the pliable surfaces are fabricated to be substantially mirror images of one another. Any manner of fastening the two surfaces together at their upper portions fall within the scope of the invention, as described, whether it be by a tab-and-lock fastening as illustrated, or by a pair of #2 or #4 screws (or otherwise) which join the pliable surfaces together—so long as the fastening method aligns the two surfaces and their apertures to be co-linear in ascertaining the true, accurate reading of the force exerted by the adhesion, and the sufficiency of the wetting of the gasket adhesives along the edge surface frame or substrate.

BRIEF DESCRIPTION OF THE DRAWINGS

These and other features of the invention will be more clearly understood from a consideration of the following description, taken in connection with the accompanying drawings, in which.

DETAILED DESCRIPTION OF THE INVENTION

Figure 1:
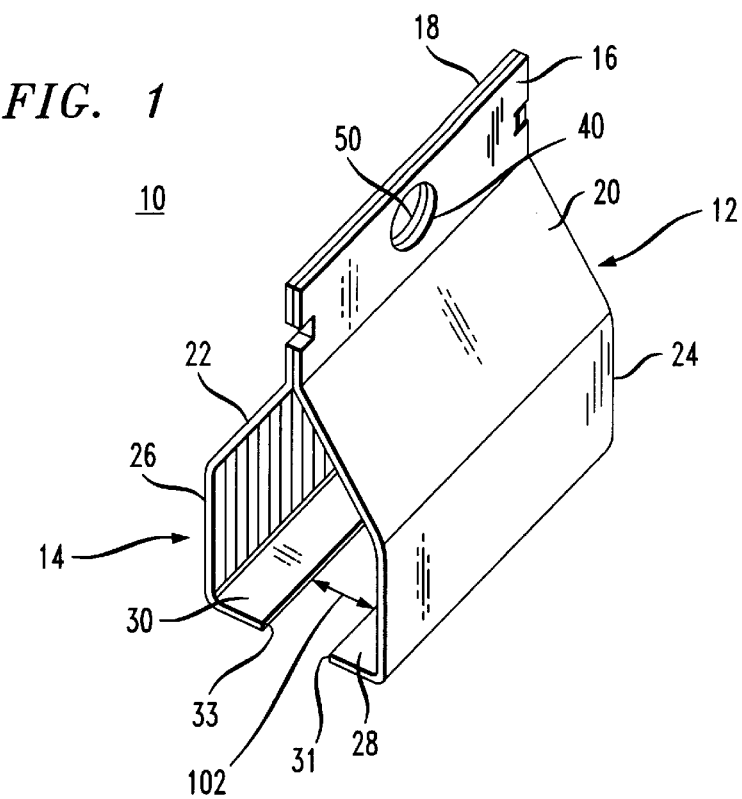
FIG. 1 is a perspective view of a preferred embodiment of a gasket adhesion test grip tool in accordance with the invention.

Referring to the drawings, the gasket adhesion test grip tool is shown at 10, as including a pair of pliable surfaces 12, 14, substantially symmetrical both in configuration and in dimension, and substantially mirror images of each other. Preferably composed of an aluminum alloy, each pliable surface includes a first section, 16, 18, a second outwardly extending second section 20, 22, a downwardly extending third section 24, 26 and an inwardly extending fourth section 28, 30. As will be understood, the sections 16 and 18 comprise the upper portion of the test grip tool; while the sections 20, 22, the sections 24, 26, and the sections 28, 30 comprise the lower portions of the tool.

Figure 2:
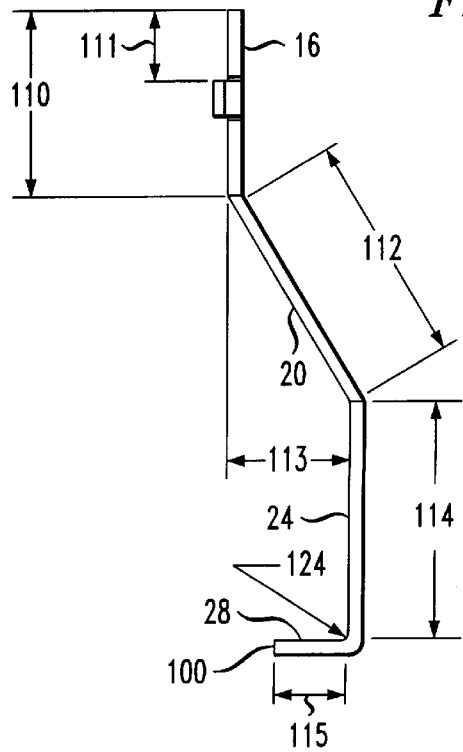
FIGS. 2–4 are side, front, and top views, respectively of one of the pair of pliable surfaces of the tool for gripping the gasket so that a force measuring gauge can be affixed to verify the wetting of the gasket adhesive according to the invention.
Figure 3:
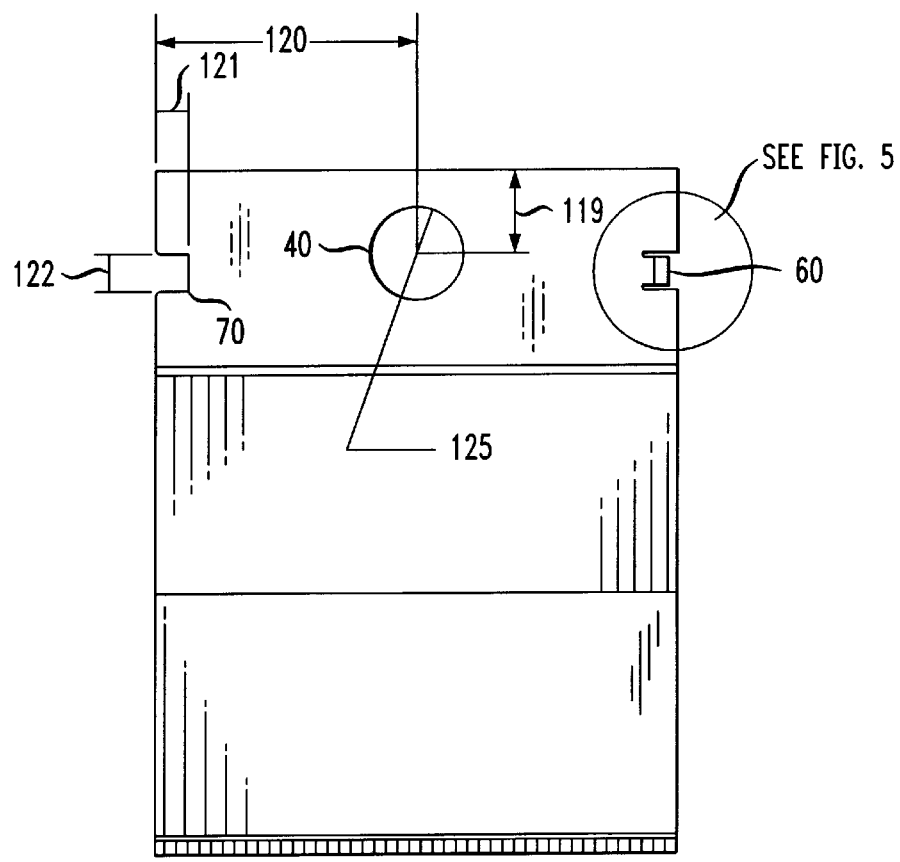
Figure 4:
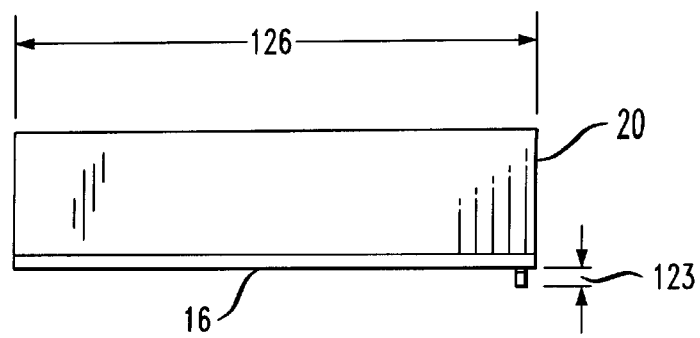
Figure 5:
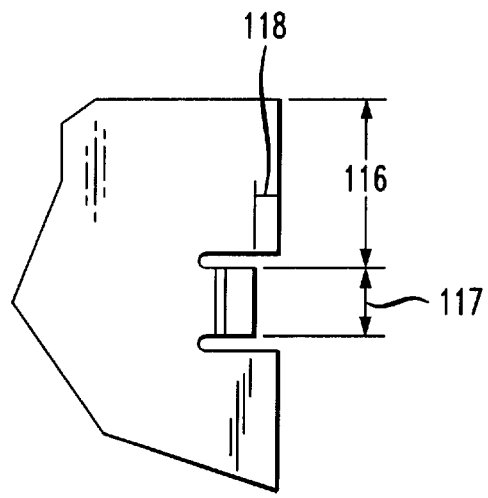
FIG. 5 is an exploded view of a detail of FIG. 3 showing a preferred manner of fastening the pair of pliable surfaces together.

As more clearly shown in FIG. 1, within each first upper portion section 16, 18, is an aperture 40, 50, which together are oriented in co-alignment when the surfaces 12, 14 are fastened together, with each aperture 40, 50 being equidistant from the facing ends 31, 33 of its respective fourth section extension 28, 30. As more clearly shown in FIG. 2, such facing ends 31, 33 extend inwardly from the third sections 24, 26, preferably at right-angles thereto. In testing the resistance of an upwardly pulling force on the adhesive carrier with the gasket rolled onto a door, panel or cabinet frame, for example, the inward facing extensions 28,30 are selected of a thickness equal to or less than the thickness of the adhesive carrier so as to permit the gasket adhesion test grip tool to be fitted under the gasket when in place. Such thickness (shown as 100 in FIG. 2) will be understood to depend upon the particular "Hollow D" gasket being tested and upon the thickness of its adhesive carrier strip. Also, in accordance with the invention, the facing ends 31, 33 of the extensions 28, 30 are separated by a distance 102 equal to or greater than the width of the adhesive carrier on the gasket—such that when the pliable surfaces 12, 14 are gripped and squeezed together, only the underside of the gasket is grasped, and not its adhesive carrier. Upward pulling upon the test grip tool 10 is thereby resisted only by the underlying adhesive carrier joined to the door, panel, cabinet, etc., the strength of which could then be read on the force measuring gauge hooked through the apertures 40, 50 in verifying the extent of the surface wetting.

Figure 6:
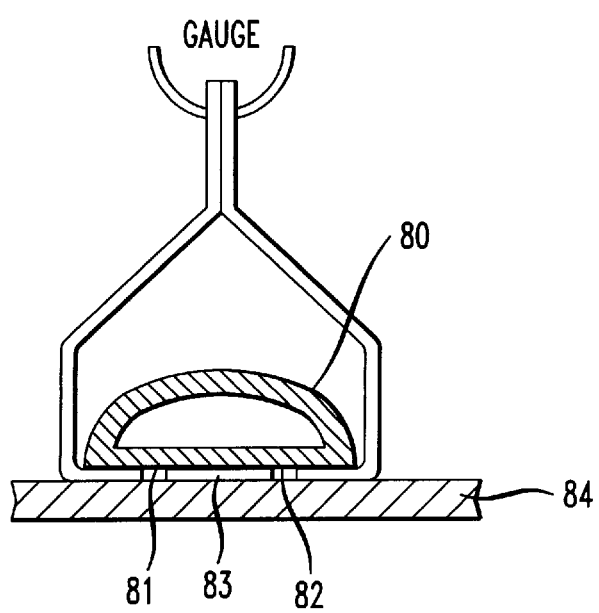
FIG. 6 is a sketch helpful in an understanding of the use of the test grip tool.

(FIG. 6 is helpful in an understanding of this, with the "Hollow D" gasket illustrated by the reference numeral 80, with its underside areas shown as 81, 82, and with its adhesive strip indicated at 83, joined with an edge surface frame 84.)

As will be appreciated, any type of appropriate fastening may be utilized to join the pliable surfaces 12, 14 together in aligning the apertures 40, 50 to be co-linear. In the embodiment of FIGS. 1–5, a foldable, or snappable tab 60 is included at one side of the downwardly extending section 16, to receive in a provided space 70 at its opposite side, a like tab from the symmetrical, mirror-like other surface 18, with its tab 60 fastening to a comparable space in such other surface, in appropriate manner, in coupling the two surfaces 16, 18 in joined arrangement. Alternatively, a pair of additional apertures can be provided, centered about the aperture 40 in FIG. 3 in the upper section 16, to receive a pair of #2 or #4 screws, for example, passing through like apertures in the opposing surface, with the screws then being fastened together by appropriately sized nuts (not shown). Such alternative arrangement will be appreciated to be consistent with the teachings of the invention, as long as the two provided screws align substantially co-linear. More specifically, the upward force provided and measured in determining the wetting sufficiency on the measuring scale will continue to be equally applied to both surfaces 12, 14 when grasping the underside areas 81, 82 of the gasket 80, so that its only resistance to separation from the door, panel or cabinet frame substrate 84 is its underlying adhesive strip 83.

While Applicants do not wish to be limited to any particular set of values, the following have proven useful in one construction of the adhesion test grip tool for a "Hollow D" gasket as provided by Chomerics Inc. of Woburn, Mass.

| Dimension 110 | 0.375 inches |
| Dimension 111 | 0.160 inches |
| Dimension 112 | 0.476 inches |
| Dimension 113 | 0.243 inches |
| Dimension 114 | 0.470 inches |
| Dimension 115 | 0.136 inches |
| Dimension 116 | 0.160 inches |
| Dimension 117 | 0.060 inches |
| Dimension 118 | 0.020 inches |
| Dimension 119 | 0.150 inches |
| Dimension 120 | 0.500 inches |
| Dimension 121 | 0.060 inches |
| Dimension 122 | 0.060 inches |
| Dimension 123 | 0.034 inches |
| Dimension 124 | 0.010 inch radius |
| Dimension 125 | 0.187 inch diameter |
| Dimension 126 | 1.000 inches |

In this embodiment of the invention, the pliable surfaces 12 and 14 of the test grip tool were fabricated of aluminum alloy, 0.020 inch thick.

While there have been described what are considered to be preferred embodiments of the present invention, it will be readily appreciated by those skilled in the art that modifications can be made without departing from the scope of the teachings herein—as, for example, utilizing a stainless steel composition for the adhesion test grip tool, instead of the aluminum alloy composition set forth, as well as modifying the dimensions to be used with alternative width "Hollow D" gaskets as may be employed. Similarly, whereas the invention has proved extremely useful in measuring the adhesion characteristics of installed "Hollow D" gaskets, the concept of employing a test grip tool of this type applies equally as well to any other gasket design having an adhesive strip carrier on the back surface underlying its central area. For at least such reasons, therefore, resort should be had to the claims appended hereto for a true understanding of the scope of the invention.

We claim:

1. A gasket adhesion test grip tool for a gasket having a given width, and an underlying adhesive carrier of given thickness and width, comprising:

a pair of pliable surfaces having upper portions fastened together and lower portions spaced apart a distance at least equal to said width of said gasket, and with each of said pair of surfaces having an inwardly facing extension at a bottom thereof of a thickness equal to or less than said thickness of said adhesive carrier for grasping an underside of said gasket when in place sealing a panel, door or cabinet frame substrate;

and means coupling a gauge to said upper portions of said pair of pliable surfaces for measuring the resistance to an upwards force pulling upon said gasket and upon said adhesive carrier.

2. The test grip tool of claim 1 wherein said means includes first and second apertures through each of said upper portions of said pair of pliable surfaces, located at a point substantially equidistant from said inwardly facing extensions of said surfaces.

3. The test grip tool of claim 2 wherein facing ends of said inwardly facing extensions of said pair of pliable surfaces are separated by a distance equal to or greater than said width of said adhesive carrier.

4. The test grip tool of claim 3 wherein said pair of pliable surfaces are substantially symmetrical in configuration and dimension.

5. The test grip tool of claim 3 wherein said pair of pliable surfaces are substantially mirror-images of each other.

6. The test grip tool of claim 3 wherein said pair of pliable surfaces are composed of an aluminum alloy composition.

7. A gasket adhesion test grip tool for a gasket having a given width, and an underlying adhesive carrier of given thickness and width, comprising:

a first surface having a first section, an outwardly extending second section joined with said first section, a downwardly extending third section joined with said second section, and an inwardly extending fourth section joined with said third section;

a second surface having a first section, an outwardly extending second section joined with said first section, a downwardly extending third section joined with said second section, and an inwardly extending fourth section joined with said third section; and means coupling a force measuring gauge to said first section of each of said first and second surfaces for the upwards pulling on said gasket having said underlying adhesive carrier sealing a panel, door or cabinet frame substrate;

with said third section of said first and second surfaces being spaced apart a distance at least equal to said width of said gasket, and with said inwardly facing fourth sections being of a thickness equal to or less than said thickness of said adhesive carrier.

8. The test grip tool of claim 7 wherein said means includes first and second apertures through said first section of said first and second surfaces, located at a point substantially equidistant from said inwardly facing fourth section of said first and second surfaces respectively.

9. The test grip tool of claim 8 wherein said inwardly facing fourth sections of said first and second surfaces are separated by a distance equal to or greater than said width of said adhesive carrier.

10. The test grip tool of claim 9 wherein said first and second surfaces are substantially symmetrical in configuration and dimension.

11. The test grip tool of claim 8 wherein said first and second surfaces are substantially mirror-images of each other.

12. The test grip tool of claim 8 wherein said first and second surfaces are composed of an aluminum alloy composition.

13. The test grip tool of claim 8 wherein said inwardly facing fourth sections of said first and second surfaces extend towards one another at substantially right-angles with respect to said downwardly extending third sections of said first and second surfaces.

14. A "Hollow D" gasket adhesion test grip tool for a "Hollow D" gasket having a given width, and an underlying adhesive carrier of given thickness and width, comprising:

a pair of pliable surfaces having upper portions fastened together and lower portions spaced apart a distance at least equal to said width of said "Hollow D" gasket, and with each of said pair of surfaces having an inwardly facing extension at a bottom thereof of a thickness equal to or less than said thickness of said adhesive carrier for grasping an underside of said gasket when in place sealing a panel, door or cabinet frame substrate;

and means coupling a gauge to said upper portions of said pair of pliable surfaces for measuring an upwards force pulling upon said gasket and upon said adhesive carrier, with said means being aligned over said carrier and substantially equidistant between opposing side areas of said gasket.

15. A "Hollow D" gasket adhesion test grip tool for a "Hollow D" gasket having a given width, and an underlying adhesive carrier of given thickness and width, comprising:

a first surface having a first section, an outwardly extending second section joined with said first section, a downwardly extending third section joined with said second section, and an inwardly extending fourth section joined with said third section;

a second surface having a first section, an outwardly extending second section joined with said first section, a downwardly extending third section joined with said second section, and an inwardly extending fourth section joined with said third section; and means coupling a gauge to said first section of each of said first and second surfaces for measuring an upwards pulling upon said "Hollow D" gasket having said underlying adhesive carrier sealing a panel, door or cabinet frame substrate;

with said means being aligned over said carrier and substantially equidistant between opposing side areas of said gasket;

and with said third section of said first and second surfaces being spaced apart a distance at least equal to said width of said gasket, and with said inwardly facing fourth sections being of a thickness equal to or less than said thickness of said adhesive carrier.

* * * * *